United States Patent
Hirokami

(10) Patent No.: US 10,442,822 B2
(45) Date of Patent: Oct. 15, 2019

(54) ORGANOSILICON COMPOUND, METHOD FOR PRODUCING SAME AND METAL SURFACE TREATMENT AGENT USING SAME

(71) Applicant: SHIN-ETSU CHEMICAL CO., LTD., Tokyo (JP)

(72) Inventor: Munenao Hirokami, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 214 days.

(21) Appl. No.: 15/519,459

(22) PCT Filed: Oct. 13, 2015

(86) PCT No.: PCT/JP2015/078872
§ 371 (c)(1),
(2) Date: Apr. 14, 2017

(87) PCT Pub. No.: WO2016/060099
PCT Pub. Date: Apr. 21, 2016

(65) Prior Publication Data
US 2017/0226136 A1  Aug. 10, 2017

(30) Foreign Application Priority Data
Oct. 17, 2014  (JP) ................. 2014-212334

(51) Int. Cl.
| | | |
|---|---|---|
| C23C 26/00 | (2006.01) |
| C07F 7/18 | (2006.01) |
| C08K 3/18 | (2006.01) |
| C07D 401/04 | (2006.01) |
| C08K 3/02 | (2006.01) |
| C08K 3/08 | (2006.01) |
| C08K 3/10 | (2018.01) |
| C08K 3/34 | (2006.01) |

(52) U.S. Cl.
CPC .............. *C07F 7/18* (2013.01); *C07D 401/04* (2013.01); *C07F 7/1804* (2013.01); *C08K 3/02* (2013.01); *C08K 3/08* (2013.01); *C08K 3/10* (2013.01); *C08K 3/18* (2013.01); *C08K 3/34* (2013.01); *C23C 26/00* (2013.01); *C08K 2003/023* (2013.01)

(58) Field of Classification Search
CPC ......... C23C 26/00; C07D 401/04; C07F 7/18; C08K 3/02; C08K 3/08; C08K 3/10; C08K 3/18; C08K 3/34; C08K 2003/023
See application file for complete search history.

(56) References Cited

U.S. PATENT DOCUMENTS

| | | | |
|---|---|---|---|
| 4,623,740 A * | 11/1986 | Deschler | C07F 7/182 544/159 |
| 5,969,019 A | 10/1999 | Kanai et al. | |
| 6,475,300 B2 | 11/2002 | Shimakura et al. | |
| 2010/0215970 A1 | 8/2010 | Imori et al. | |
| 2010/0233470 A1* | 9/2010 | Sasaki | C09D 123/0853 428/327 |

FOREIGN PATENT DOCUMENTS

| | | | |
|---|---|---|---|
| JP | 61-18792 A | 1/1986 |
| JP | 6-279463 A | 10/1994 |
| JP | 8-73775 A | 3/1996 |
| JP | 10-60315 A | 3/1998 |
| JP | 11-29724 A | 2/1999 |
| JP | 2000-297093 A | 10/2000 |
| JP | 2001-316845 A | 11/2001 |
| JP | 2007-297648 A | 11/2007 |
| JP | 2013-194258 A | 9/2013 |
| WO | WO 2009-038135 A1 | 3/2009 |

OTHER PUBLICATIONS

International Search Report issued in PCT/JP2015/078872 (PCT/ISA/210), dated Dec. 22, 2015.
Written Opinion of the International Searching Authority issued in PCT/JP2015/078872 (PCT/ISA/237), dated Dec. 22, 2015.

* cited by examiner

*Primary Examiner* — Bijan Ahvazi
(74) *Attorney, Agent, or Firm* — Birch, Stewart, Kolasch & Birch, LLP

(57) ABSTRACT

An organosilicon compound represented by general formula (1). The present invention is able to provide an organosilicon compound which has excellent adhesion during processing and high bonding strength, while exhibiting antirust corrosion resistance at high levels, and which is useful as a metal surface treatment agent.

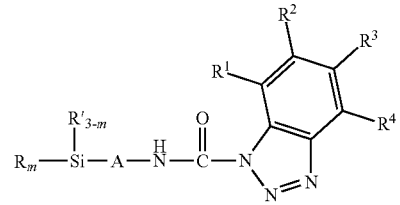

(1)

(In the formula, R represents a hydrolyzable group; R' represents an alkyl group; A represents an alkylene group; $R^1$ and $R^2$, $R^2$ and $R^3$, or $R^3$ and $R^4$ among the $R^1$, $R^2$, $R^3$ and $R^4$ moieties may combine together to form an aliphatic or aromatic ring skeleton, and in cases where a ring skeleton is not formed, each one of the $R^1$, $R^2$, $R^3$ and $R^4$ moieties independently represents a hydrogen atom or an alkyl group; and m represents a number of 1-3.)

2 Claims, No Drawings

ORGANOSILICON COMPOUND, METHOD FOR PRODUCING SAME AND METAL SURFACE TREATMENT AGENT USING SAME

TECHNICAL FIELD

This invention relates to metal surface treating compositions which are useful for the surface treatment of a variety of steel members including copper plate, cold rolled steel, hot rolled steel, stainless steel, and plated steel members such as zinc electroplated steel, hot dip galvanized steel, zinc-aluminum alloy plated steel, zinc-iron alloy plated steel, zinc-magnesium alloy plated steel, zinc-aluminum-magnesium alloy plated steel, aluminum plated steel, aluminum-silicon alloy plated steel, tin plated steel, lead-tin alloy plated steel, chromium plated steel, and nickel plated steel; steel members surface treated therewith; a method for the surface treatment of steel members; and a method for producing coated steel members having an overcoat layer on the treated steel surface.

BACKGROUND ART

For the metal surface treatment, chromium-based surface treating agents such as chromate and phosphate/chromate agents are known in the art and are widely utilized even at the present. However, the recent trend of environmental regulations suggests an upcoming possibility to ban the chromium-based surface treating agents because of the toxicity and especially carcinogenicity of chromium. There is a desire to have a metal surface treating agent that is free of chromium and that achieves adhesion and corrosion resistance comparable to the chromate treating agents.

JP-A H11-29724 (Patent Document 1) proposes a non-chromate treating agent for rust prevention comprising a water-soluble resin, a thiocarbonyl-containing compound and a phosphate ion and optionally water dispersible silica. This system is improved in corrosion resistance, but lacks workability and adhesion to substrates. JP-A H08-073775 (Patent Document 2) discloses an acidic surface treating agent comprising at least two silane coupling agents. This system is short of corrosion resistance where high corrosion resistance and workability are required after the metal surface treatment.

In connection with these, JP-A 2001-316845 (Patent Document 3) discloses a non-chromate, metal surface treating agent comprising a silane coupling agent, water dispersible silica, and zirconium or titanium ion as essential components. Corrosion resistance and workability are improved, but coating to substrates and bond strength to an overcoat layer are still insufficient.

JP-A H10-60315 (Patent Document 4) discloses a surface treating agent for steel structures comprising a silane coupling agent having a specific functional group capable of reacting with an aqueous emulsion. In this case, only corrosion resistance to relatively mild tests like a humidity cabinet test is required. This agent is short of corrosion resistance as compared with the metal surface treating agent that withstands rigorous corrosion tests as contemplated in the present invention.

JP-A 2000-297093 (Patent Document 5) describes that an imidazole-containing organosilicon compound is used as a surface treating agent for metals. The surface treating agent is still unsatisfactory in corrosion resistance and deep drawing resistance. JP-A H06-279463 (Patent Document 6) describes that a benzotriazole-containing organosilicon compound is used as a surface treating agent for metals. This surface treating agent is likewise unsatisfactory in corrosion resistance and deep drawing resistance.

JP-A 2007-297648 (Patent Document 7) discloses a rust preventive surface treating agent comprising an aqueous emulsion, a compound having a trivalent transition metal ion coordinated with two molecules of β-diketone and two molecules of water, and a silane coupling agent. The surface treating agent is characterized in that the trivalent transition metal complex converts to a substantially insoluble compound on drying, exerting rust prevention and adhesion of an overcoat. The required level of corrosion resistance is not resistance against a rigorous environment as contemplated in the present invention. There is left room for further improvement.

Accordingly, there exists a desire to have a metal surface treating agent which in thin film form develops high levels of properties including corrosion resistance, work adhesion, coating and bond strength.

PRIOR ART DOCUMENTS

Patent Documents

Patent Document 1: JP-A H11-29724
Patent Document 2: JP-A H08-073775
Patent Document 3: JP-A 2001-316845
Patent Document 4: JP-A H10-60315
Patent Document 5: JP-A 2000-297093
Patent Document 6: JP-A H06-279463
Patent Document 7: JP-A 2007-297648

SUMMARY OF THE INVENTION

Problems to be Solved by the Invention

An object of the invention, which has been made under the above-mentioned circumstances, is to provide an organosilicon compound suited as a non-chromate surface treating composition which is free of chromium, which is advantageously used for the treatment of metals, especially metal-coated steel members, and which is capable of imparting excellent workability, adhesion and corrosion resistance when used in pretreatment prior to coating with coating materials; and a method for producing the same. Another object is to provide a metal surface treating composition using the organosilicon compound, steel members surface treated therewith, a method for the surface treatment of steel members, coated steel members having an overcoat layer on the treated steel surface, and a method for producing the coated steel members.

Means for Solving the Problems

To attain the above object, the invention provides an organosilicon compound, a method for producing the same, metal surface treating compositions, steel members surface treated therewith, a method for the surface treatment of steel members, coated steel members, and a method for producing coated steel members, as defined below.

[1] An organosilicon compound having the general formula (1):

[Chemical Formula 1]

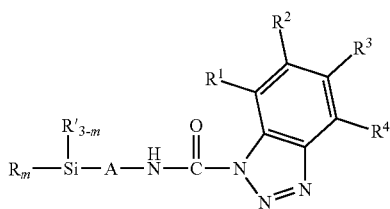

(1)

wherein R is a hydrolyzable group, R' is a $C_1$-$C_4$ alkyl group, A is a $C_1$-$C_8$ alkylene group, $R^1$, $R^2$, $R^3$ and $R^4$ are each independently hydrogen or a $C_1$-$C_6$ alkyl group when they do not form a ring structure, or a pair of $R^1$ and $R^2$, $R^2$ and $R^3$, or $R^3$ and $R^4$ may bond together to form an aliphatic or aromatic ring structure, and m is an integer of 1 to 3.

[2] The organosilicon compound of claim 1, having the general formula (2):

[Chemical Formula 2]

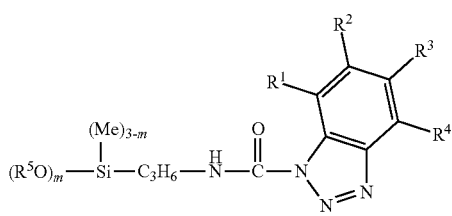

(2)

wherein $R^5$ is a $C_1$-$C_{10}$ alkyl or $C_6$-$C_{10}$ aryl group, $R^1$, $R^2$, $R^3$, $R^4$ and m are as defined above, and Me is methyl.

[3] A method for producing the organosilicon compound of [1] or [2], comprising the step of reacting an organosilicon compound having the general formula (3):

[Chemical Formula 3]

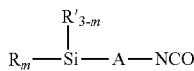

(3)

wherein R, R', A and m are as defined above, with a benzotriazole compound having the general formula (4):

[Chemical Formula 4]

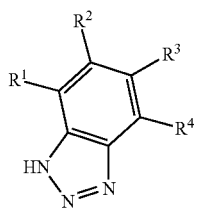

(4)

wherein $R^1$, $R^2$, $R^3$ and $R^4$ are as defined above.

[4] A metal surface treating composition comprising the organosilicon compound of [2] or [2] as an active ingredient.

[5] The metal surface treating composition of [4], further comprising an alkoxysilane having the general formula (13) or a partial hydrolytic condensate thereof, $$R^6_x Si(OR^7)_{4-x} \quad (13)$$

wherein $R^6$ is a substituted or unsubstituted, $C_1$-$C_{20}$ monovalent hydrocarbon group, $R^7$ is a substituted or unsubstituted, $C_1$-$C_8$ monovalent hydrocarbon group, and x is an integer of 0 to 3.

[6] The metal surface treating composition of [4] or [5], further comprising an organic titanate.

[7] The metal surface treating composition of any one of [4] to [6], further comprising water dispersible silica or organic solvent dispersible silica.

[8] The metal surface treating composition of any one of [4] to [7], further comprising a compound of at least one metal selected from the group consisting of Fe, Zr, Ti, V, W, Mo, Al, Sn, Nb, Hf, Y, Ho, Bi, La, Ce, and Zn.

[9] The metal surface treating composition of any one of [4] to [8], further comprising a thiocarbonyl-containing compound.

[10] The metal surface treating composition of any one of [4] to [9], further comprising a water soluble or water dispersible resin.

[11] The metal surface treating composition of any one of [4] to [10], further comprising a phosphate ion.

[12] A method for the surface treatment of a steel member, comprising the step of treating a surface of a steel member with the metal surface treating composition of any one of [4] to [11].

[13] A method for preparing a coated steel member, comprising the steps of treating a steel member with the metal surface treating composition of any one of [4] to [11] and forming an overcoat layer on the treated member.

[14] A surface-treated steel member obtained by the surface treating method of [12].

[15] A coated steel member obtained by the preparation method of [13].

Advantageous Effects of the Invention

The organosilicon compound of the invention is a silane coupling agent having a benzotriazole group and a urea group. The metal surface treating composition containing the organosilicon compound as an essential component displays good rust prevention because a substantially insoluble complex forms by means of coordination of the benzotriazole group and urea group of the silane coupling agent to the treated metal member. By virtue of a hydrolyzable silyl group on the organosilicon compound, work adhesion to a substrate and an organic or inorganic resin overcoat layer optionally applied on the treated surface is improved, leading to enhanced bond strength. Therefore, the coated steel member exhibits a high level of rust prevention or corrosion resistance.

Embodiment for Carrying Out the Invention

Below the invention is described in more detail.
The invention provides an organosilicon compound having a benzotriazole group and a urea group, and a metal surface treating composition comprising the organosilicon compound as an essential component, which is dissolved in water, an organic solvent or a mixture of water and an organic solvent.

[Organosilicon Compound]

The organosilicon compound of the invention has the general formula (1).

[Chemical Formula 5]

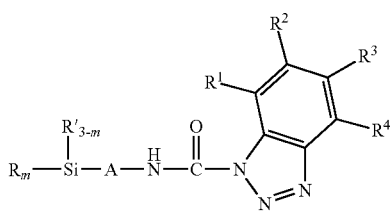
(1)

Herein R is a hydrolyzable group, R' is a $C_1$-$C_4$ alkyl group, A is a $C_1$-$C_8$ alkylene group, $R^1$, $R^2$, $R^3$ and $R^4$ are each independently hydrogen or a $C_1$-$C_6$ alkyl group when they do not form a ring structure, or a pair of $R^1$ and $R^2$, $R^2$ and $R^3$, or $R^3$ and $R^4$ may bond together to form an aliphatic or aromatic ring structure, and m is an integer of 1 to 3.

The preferred organosilicon compound has the general formula (2).

[Chemical Formula 6]

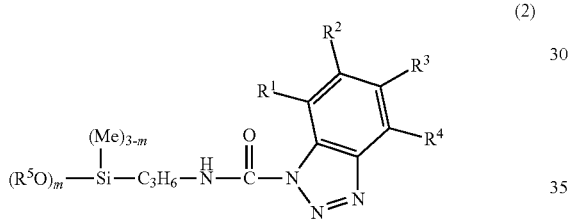
(2)

Herein $R^5$ is a $C_1$-$C_{10}$ alkyl or $C_6$-$C_{10}$ aryl group, $R^1$, $R^2$, $R^3$, $R^4$ and m are as defined above, and Me is methyl.

Examples of R include halogen atoms such as chlorine and bromine, and alkoxy groups such as methoxy and ethoxy. Of these, the alkoxy group is preferred, with methoxy being most preferred. Examples of R' include alkyl groups such as methyl, ethyl and propyl, with methyl being preferred. Examples of A include methylene, ethylene, propylene, hexylene, and octylene. Preferably, A is a linear $C_1$-$C_3$ alkylene group, most preferably propylene. Examples of $R^1$, $R^2$, $R^3$ and $R^4$ include hydrogen and alkyl groups such as methyl, ethyl, propyl, isopropyl, butyl and isobutyl, and examples of the ring structure formed by a pair of bonding $R^1$ and $R^2$, $R^2$ and $R^3$, or $R^3$ and $R^4$ include cyclohexane and benzene rings. The letter m is an integer of 1 to 3, preferably 2 or 3, and most preferably 3.

It is preferred from the economic aspect that the inventive organosilicon compounds be organosilicon compounds (5) to (12).

[Chemical Formula 7]

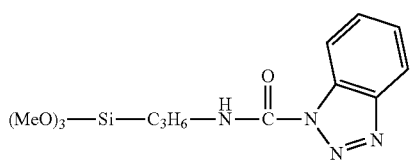
(5)

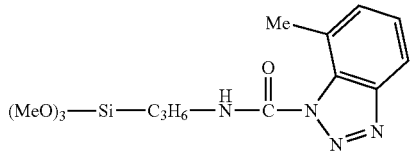
(6)

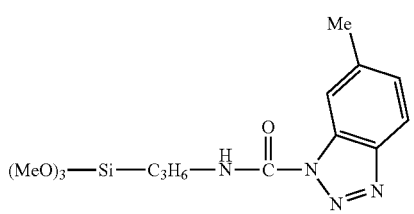
(7)

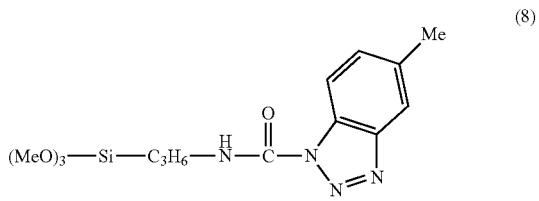
(8)

[Chemical Formula 8]

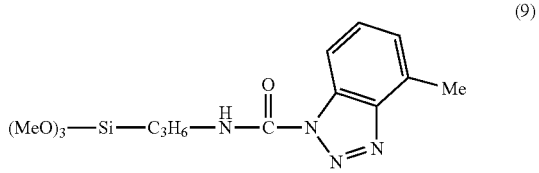
(9)

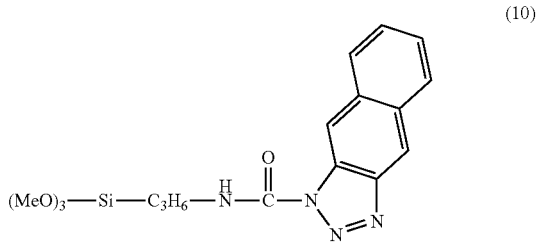
(10)

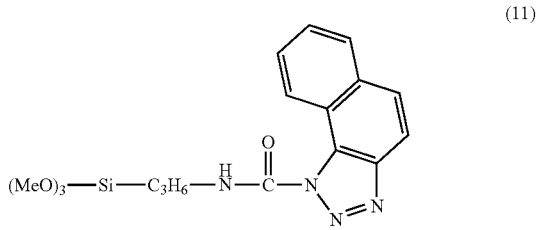
(11)

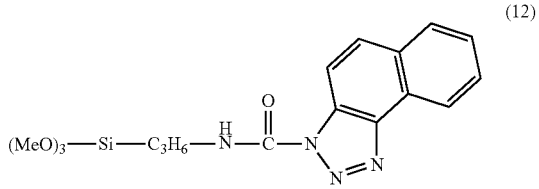
(12)

[Method of Synthesizing Organosilicon Compound]

The inventive organosilicon compound is obtained by reacting an organosilicon compound having the general formula (3):

[Chemical Formula 9]

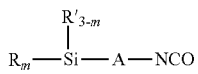

(3)

wherein R, R', A and m are as defined above, with a benzotriazole compound having the general formula (4):

[Chemical Formula 10]

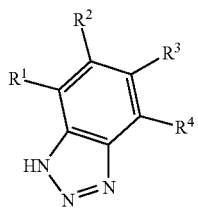

(4)

wherein $R^1$, $R^2$, $R^3$ and $R^4$ are as defined above.

Examples of the organosilicon compound of formula (3) include 3-isocyanatopropyltrimethoxysilane, 3-isocyanatopropyltriethoxysilane, 3-isocyanatopropylmethyldimethoxysilane, and 3-isocyanatopropylmethyldiethoxysilane.

Examples of the benzotriazole compound of formula (4) include benzotriazole, 3-methylbenzotriazole, 4-methylbenzotriazole, 5-methylbenzotriazole, 6-methylbenzotriazole, 1H-naphtho[2,3]triazole, and 1H-naphtho[1,2]triazole.

Although the ratio of the benzotriazle compound of formula (4) to the organosilicon compound of formula (3) may be properly selected, the benzotriazle compound of formula (4) is preferably used in an amount of 0.5 to 1.5 moles, more preferably 0.8 to 1.2 moles per mole of the organosilicon compound of formula (3).

A solvent may be used in the production of the inventive organosilicon compound, if desired. The solvent is not particularly limited as long as it is nonreactive with the reactants, isocyanate-containing organosilicon compound and benzotriazole compound. Exemplary solvents include aliphatic hydrocarbon solvents such as pentane, hexane, heptane and decane, ether solvents such as diethyl ether, tetrahydrofuran and 1,4-dioxane, amide solvents such as formamide, dimethylformamide and N-methylpyrrolidone, and aromatic hydrocarbon solvents such as benzene, toluene and xylene.

A catalyst may be used in the production of the inventive organosilicon compound, if desired. The catalyst may be selected from commonly used isocyanate reaction catalysts, preferably tin compounds. Inter alia, tin (II) carboxylate compounds are more preferred for catalytic activity. The amount of the catalyst used is preferably 1 to 0.00001 mole, more preferably 0.01 to 0.0001 mole per mole of the isocyanate monomer. More than 1 mole of the catalyst may be uneconomical because the effect is saturated. If the amount is less than 0.00001 mole, the catalytic effect may be insufficient, resulting in a slow reaction rate and a decline of productivity.

The reaction to produce the inventive organosilicon compound is exothermic. Since side reactions can occur at unnecessarily high temperatures, the reaction temperature is preferably controlled in a range of 20° C. to 150° C., more preferably 30° C. to 130° C., and even more preferably 40° C. to 110° C. Below 20° C., the reaction rate may be retarded, resulting in a decline of productivity. Above 150° C., side reactions such as polymerization of the isocyanate monomer may take place.

The reaction time required to produce the inventive organosilicon compound is not particularly limited as long as the above-mentioned temperature control during exothermic reaction is possible and the exothermic reaction is brought to completion. The reaction time is preferably about 10 minutes to about 24 hours, more preferably about 1 hour to about 10 hours.

[Metal Surface Treating Composition]

The invention provides a metal surface treating composition comprising an organosilicon compound of formula (1) as an active component.

[Chemical Formula 11]

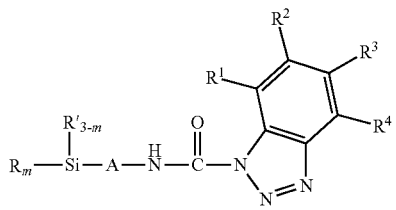

(1)

Herein R, R', A, $R^1$, $R^2$, $R^3$, $R^4$ and m are as defined above.

More preferably, the metal surface treating composition contains an organosilicon compound of formula (2) as an active component.

[Chemical Formula 12]

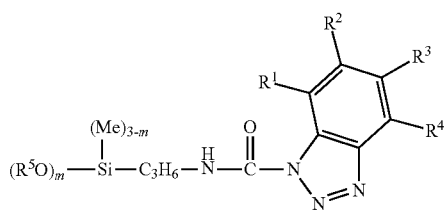

(2)

Herein $R^1$, $R^2$, $R^3$, $R^4$, $R^5$, Me and m are as defined above.

It is preferred from the economic aspect that the organosilicon compounds used in the metal surface treating composition be the foregoing organosilicon compounds (5) to (12).

The metal surface treating composition may contain another component which is water, an organic solvent in which the organosilicon compound is dissolvable, or a mixture of water and the organic solvent. Suitable organic solvents include alcohol solvents such as methanol and ethanol, amide solvents such as formamide, N,N-dimethylformamide, pyrrolidone and N-methylpyrrolidone, ketone solvents such as acetone, methyl ethyl ketone and methyl isobutyl ketone, saturated hydrocarbon solvents such as pentane, hexane and heptane, and aromatic hydrocarbon solvents such as benzene, toluene and xylene. Inter alia, methanol and ethanol are preferred. The organic solvents are not limited to those listed herein.

The metal surface treating composition preferably contains the organosilicon compound of formulae (1) to (12) in a concentration of 0.01 to 200 g/L, more preferably 0.05 to 100 g/L. Too low contents of the compound may achieve least effects whereas too high contents may reduce the liquid stability of coating material.

Besides the organosilicon compounds of formulae (1) to (12), preferably the metal surface treating composition may further contain another organosilicon compound. The other organosilicon compound is not particularly limited as long as it is a compound having a hydrolyzable silyl group other than the organosilicon compounds of formulae (1) to (12). Preferred are organosilicon compounds having a hydrolyzable silyl group, represented by the general formula (13) or a partial hydrolytic condensate thereof.

$$R^6{}_x Si(OR^7)_{4-x} \quad (13)$$

Herein $R^6$ is a substituted or unsubstituted monovalent hydrocarbon group of 1 to 20 carbon atoms, especially 1 to 15 carbon atoms, $R^7$ is a substituted or unsubstituted monovalent hydrocarbon group of 1 to 8 carbon atoms, especially 1 to 6 carbon atoms, $R^6$ and $R^7$ are preferably methyl or ethyl, and x is an integer of 0 to 3, more preferably 0 to 2.

Examples of the unsubstituted monovalent hydrocarbon group include alkyl groups such as methyl, ethyl and propyl, alkenyl groups such as vinyl and allyl, aryl groups such as phenyl and tolyl, and aralkyl groups such as benzyl. Examples of the substituted monovalent hydrocarbon group include substituted forms of unsubstituted monovalent hydrocarbon groups such as alkyl in which one or more hydrogen atoms are substituted by epoxy, (meth)acryloxy, mercapto, amino, aminoalkylamino, alkylamino, isocyanate, polyether, halogen or perfluoropolyether.

Examples include tetramethoxysilane, tetraethoxysilane, methyltrimethoxysilane, methyltriethoxysilane, dimethyldimethoxysilane, dimethyldiethoxysilane, trimethylmethoxysilane, trimethylethoxysilane, phenyltrimethoxysilane, phenyltriethoxysilane, phenylmethyldimethoxysilane, phenylmethyldiethoxysilane, phenyldimethylmethoxysilane, phenyldimethylethoxysilane, diphenyldimethoxysilane, diphenyldiethoxysilane, vinyltrimethoxysilane, vinyltriethoxysilane, vinylmethyldimethoxysilane, vinylmethyldiethoxysilane, γ-glycidoxypropyltrimethoxysilane, γ-glycidoxypropyltriethoxysilane, γ-glycidoxypropylmethyldimethoxysilane, γ-glycidoxypropylmethyldiethoxysilane, γ-(meth)acryloxypropyltrimethoxysilane, γ-(meth)acryloxypropyltriethoxysilane, γ-(meth)acryloxypropylmethyldimethoxysilane, γ-(meth)acryloxypropylmethyldiethoxysilane, 3-mercaptopropyltrimethoxysilane, 3-mercaptopropyltriethoxysilane, 3-mercaptopropylmethyldimethoxysilane, 3-mercaptopropylmethyldiethoxysilane, 3-aminopropyltrimethoxysilane, 3-aminopropyltriethoxysilane, 3-aminopropylmethyldimethoxysilane, 3-aminopropylmethyldiethoxysilane, N-aminoethyl-γ-aminopropyltrimethoxysilane, N-aminoethyl-γ-aminopropyltriethoxysilane, N-aminoethyl-γ-aminopropylmethyldimethoxysilane, N-aminoethyl-γ-aminopropylmethyldiethoxy silane, γ-isocyanatopropyltrimethoxysilane, γ-isocyanatopropyltriethoxysilane, γ-isocyanatopropylmethyldimethoxysilane, γ-isocyanatopropylmethyldiethoxysilane, 3-chloropropyltrimethoxysilane, 3-chloropropyltriethoxysilane, 3-chloropropylmethyldimethoxysilane, 3-chloropropylmethyldiethoxysilane, 2-(3,4-epoxycyclohexyl)ethyltrimethoxysilane, 2-(3,4-epoxycyclohexyl)ethyltriethoxysilane, 2-(3,4-epoxycyclohexyl)ethylmethyldimethoxysilane, and 2-(3,4-epoxycyclohexyl)ethylmethyldiethoxysilane.

When the other organosilicon compound is compounded in the metal surface treating composition, it is preferably present in a concentration of 0.05 to 100 g/L, more preferably 0.5 to 60 g/L. If the content is less than 0.05 g/L, corrosion resistance may be poor. If the content exceeds 100 g/L, corrosion resistance may be saturated and productivity may decline.

Preferably the metal surface treating composition may further contain an organic titanate. The organic titanate is not particularly limited in structure or the like, and commercially available one may be used. Examples of the organic titanate include tetraethyl titanate, tetraisopropyl titanate, tetra-n-butyl titanate, butyl titanate dimer, tetra(2-ethylhexyl) titanate, and polymers thereof. Also included are titanium chelate compounds such as titanium acetyltitanate, poly(titanium acetylacetonate), titanium octylglycinate, titanium lactate, titanium ethyl lactate, and titanium triethanolaminate. These titanates may be used alone or in admixture of two or more.

When the organic titanate is compounded in the metal surface treating composition, it is preferably present in a concentration of 0.05 to 100 g/L, more preferably 0.5 to 60 g/L. If the content is less than 0.05 g/L, corrosion resistance may be poor. If the content exceeds 100 g/L, corrosion resistance may be saturated and inversely, the bath stability of the metal surface treating composition may be reduced.

Preferably the metal surface treating composition may further contain a water or organic solvent dispersible silica. Although the water or organic solvent dispersible silica is not particularly limited, preference is given to spherical silica, chain-like silica and aluminum-modified silica because of less impurities such as sodium and weak alkalinity. Examples of the spherical silica include colloidal silica such as Snowtex N and Snowtex UP (both from Nissan Chemical Industries, Ltd.) and fumed silica such as Aerosil (Nippon Aerosil Co., Ltd.). Exemplary of the chain-like silica is silica gel such as Snowtex PS (Nissan Chemical Industries, Ltd.). Exemplary of the aluminum-modified silica is silica gel such as Adelite AT-20A (Asahi Denka Kogyo K.K). Any of such commercially available silica and silica gel may be used.

Examples of the organic solvent include alcohols such as methanol, ethanol and isopropanol and ether compounds such as propylene glycol monomethyl ether and tetrahydrofuran.

When the water or organic solvent dispersible silica is compounded in the metal surface treating composition, it is preferably present in a concentration of 0.05 to 100 g/L, more preferably 0.5 to 60 g/L, calculated as solids. If the content of the silica is less than 0.05 g/L, corrosion resistance may be poor. If the content exceeds 100 g/L, no further corrosion resistance-improving effect may be observed and inversely, the bath stability of the metal surface treating composition may be reduced.

Preferably the metal surface treating composition may further contain a compound of at least one metal selected from among Fe, Zr, Ti, V, W, Mo, Al, Sn, Nb, Hf, Y, Ho, Bi, La, Ce, and Zn. Examples include carbonates, oxides, hydroxides, nitrates, sulfates, phosphates, fluorides, fluoro acids and salts thereof, oxoacid salts, and organic acid salts of these metals.

More specifically, examples of the zirconium (Zr) compound include ammonium zirconium carbonate, fluorozirconic acid, ammonium fluorozirconate, potassium fluorozirconate, sodium fluorozirconate, zirconium acetylacetonate, 1-butanol solution of zirconium butoxide, and zirconium n-propoxide.

Examples of the titanium (Ti) compound include fluorotitanic acid, ammonium fluorotitanate, potassium titanium oxalate, titanium isopropoxide or isopropyl titanate, titanium ethoxide, titanium-2-ethyl-1-hexanolate, tetraisopropyl titanate, tetra-n-butyl titanate, potassium fluorotitanate, and sodium fluorotitanate.

Examples of the vanadium (V) compound include vanadium(V) pentoxide, vanadium(III) trioxide, vanadium(IV) dioxide, vanadium(II) hydroxide, vanadium(III) hydroxide, vanadium(II) sulfate, vanadium(III) sulfate, vanadium(IV) oxysulfate, vanadium(III) fluoride, vanadium(IV) fluoride, vanadium(V) fluoride, vanadium oxytrichloride $VOCl_3$, vanadium trichloride $VCl_3$, hexafluorovanadic acid(III) and salts thereof (e.g., potassium and ammonium salts), metavanadic acid (V) and salts thereof (e.g., sodium and ammonium salts), vanadyl(IV) acetylacetonate $VO(OC(=CH_2)CH_2COCH_3)_2$, vanadium(III) acetylacetonate $V(OC(=CH_2)CH_2COCH_3)_3$, and phosphor-vanado-molybdic acid $H_{15-X}[PV_{12-X}MoO_{40}] \cdot nH_2O$ (6<X<12, n<30).

Examples of the tungsten (W) compound include tungsten (IV) oxide, tungsten(V) oxide, tungsten(VI) oxide, tungsten (IV) fluoride, tungsten(VI) fluoride, tungstic acid(VI) $H_2WO_4$ and salts thereof (e.g., ammonium and sodium salts), metatungstic acid(VI) $H_6[H_2W_{12}O_{40}]$ and salts thereof (e.g., ammonium and sodium salts), and paratungstic acid(VI) $H_{10}[H_{10}W_{12}O_{46}]$ and salts thereof (e.g., ammonium and sodium salts).

Examples of the molybdenum (Mo) compound include phosphor-vanado-molybdic acid $H_{15-X}[PV_{12-X}MoO_{40}] \cdot nH_2O$ (6<X<12, n<30), molybdenum oxide, molybdic acid $H_2MoO_4$, ammonium molybdate, ammonium paramolybdate, sodium molybdate, molybdophosphate compounds (e.g., anmonium molybdophosphate $(NH_4)_3[PO_4Mo_{12}O_{36}] \cdot 3H_2O$, and sodium molybdophosphate $Na_3[PO_4Mo_{12}O_{36}] \cdot nH_2O$.

Examples of the aluminum (Al) compound include aluminum nitrate, aluminum sulfate, aluminum potassium sulfate, aluminum sodium sulfate, aluminum ammonium sulfate, aluminum phosphate, aluminum carbonate, aluminum oxide, and aluminum hydroxide.

Examples of the tin (Sn) compound include tin(IV) oxide, sodium stannate $Na_2SnO_3$, tin(II) chloride, tin(IV) chloride, tin(II) nitrate, tin(IV) nitrate, and ammonium hexafluorostannate $(NH_4)_2SnF_6$.

Examples of the niobium (Nb) compound include niobium pentoxide $Nb_2O_5$, sodium niobate $NaNbO_3$, niobium fluoride $NbF_5$, and ammonium hexafluoroniobate $(NH_4)_2NbF_6$.

Examples of the hafnium (Hf) compound, yttrium (Y) compound, holmium (Ho) compound, bismuth (Bi) compound and lanthanum (La) compound include hafnium oxide, hexafluorohafnic acid, yttrium oxide, yttrium acetylacetonate, holmium oxide, bismuth oxide, and lanthanum oxide.

Examples of the cerium (Ce) compound include cerium oxide, cerium acetate $Ce(CH_3CO_2)_3$, cerium(III) or (IV) nitrate, ammonium cerium nitrate, cerium sulfate, and cerium chloride.

Examples of the zinc (Zn) compound include zinc oxide, zinc hydroxide, zinc acetate, zinc nitrate, zinc sulfate, zinc chloride, and sodium zincate.

These metal compounds may be used alone or in admixture of two or more.

When the metal compound is compounded in the metal surface treating composition, it is preferably present in a concentration of 0.01 to 50 g/L, more preferably 0.05 to 5 g/L, calculated as metal ion. If the content of the metal compound is less than 0.01 g/L, corrosion resistance may be poor. If the content exceeds 50 g/L, the work adhesion improving effect may be lost and inversely, the bath stability may be reduced.

Preferably the metal surface treating composition may further contain a thiocarbonyl-containing compound. The thiocarbonyl-containing compound is a compound having at least one thiocarbonyl group, examples of which include thiourea, dimethylthiourea, 1,3-dimethylthiourea, dipropylthiourea, dibutylthiourea, 1,3-diphenyl-2-thiourea, 2,2-ditolylthiourea, thioacetamide, sodium dimethyldithiocarbamate, tetramethylthiuram monosulfide, tetrabutylthiuram disulfide, zinc N-ethyl-N-phenyldithiocarbamate, zinc dimethyldithiocarbamate, piperidine pentamethylenedithiocarbamate, zinc diethyldithiocarbamate, sodium diethyldithiocarbamate, zinc isopropylxanthate, ethylene thiourea, dimethylxanthate sulfide, dithiooxamide, polydithiocarbamic acid and salts thereof. These compounds may be used alone or in admixture of two or more.

When the thiocarbonyl-containing compound is compounded in the metal surface treating composition, it is preferably present in a concentration of 0.01 to 100 g/L, more preferably 0.1 to 10 g/L. If the content of the compound is less than 0.01 g/L, corrosion resistance may be poor. More than 100 g/L of the compound may be uneconomical because corrosion resistance may be saturated.

The metal surface treating composition may further contain a water soluble or water dispersible resin. Examples of the water soluble or water dispersible resin include acrylic resins, epoxy resins, urethane resins, ethylene-acrylic copolymers, phenolic resins, polyester resins, polyolefin resins, alkyd resins, and polycarbonate resins. These resins may be used alone or in admixture of two or more or even in a copolymerized form. For example, the water soluble acrylic resins are copolymers based on acrylate and/or methacrylate such as methyl acrylate, ethyl acrylate, methyl methacrylate, and ethyl methacrylate, and derivatives thereof while copolymers with other acrylic monomers may also be used. Those copolymers containing at least 70 wt % of the acrylate and/or methacrylate monomer are preferred.

When the resin is compounded, an organic solvent may be used together to improve the film-forming ability of the resin in order to form a more uniform smooth coating film. There may also be compounded surfactants, leveling agents, wettability improvers, and antifoaming agents.

The water soluble or water dispersible resin has a molecular weight of at least 10,000, preferably 300,000 to 2,000,000, as a weight average molecular weight measured by gel permeation chromatography (GPC) versus polystyrene standards. If the molecular weight is less than 10,000, the effects of the invention, especially effect of improving deep drawing resistance of a coating film may not be fully exerted. If the molecular weight exceeds 2,000,000, the composition may have a high viscosity and be low in handling efficiency.

When the water soluble or water dispersible resin is compounded in the metal surface treating composition, it is preferably present in a concentration of 0.1 to 100 g/L, more preferably 5 to 80 g/L. If the concentration of the resin is less than 0.1 g/L, the effects of improving bend-following adhesion and deep drawing resistance may be poor. More than 100 g/L of the resin may be uneconomical because the effects of improving bend-following adhesion and deep drawing resistance may be saturated.

Preferably the metal surface treating composition may further contain a phosphate ion. Addition of phosphate ion may further improve corrosion resistance. The phosphate ion may be introduced by adding a compound capable of providing a phosphate ion in water. Examples of the compound include phosphoric acid, phosphates such as $Na_3PO_4$, $Na_2HPO_4$ and $NaH_2PO_4$, and condensed phosphoric acids such as polyphosphoric acid, metaphosphoric acid and diphosphoric acid and salts thereof. These compounds may be used alone or in admixture of two or more.

When the phosphate ion is compounded in the metal surface treating composition, it is preferably present in a concentration of 0.01 to 100 g/L, more preferably 0.1 to 10 g/L. If the amount of the phosphate ion added is less than 0.01 g/L, the corrosion resistance improving effect may be poor. More than 100 g/L of the phosphate ion may cause excessive etching to zinc-plated steel to deprive it of performance, or cause gelation to the composition which contains a water soluble resin as an optional component.

The metal surface treating composition may further contain additives well known as metal surface treating agents. Examples include tannic acid and salts thereof, phytic acid and salts thereof.

The metal surface treating compositions of the invention are useful for the surface treatment of a variety of steel members including copper plate, cold rolled steel, hot rolled steel, stainless steel, zinc electroplated steel, hot dip galvanized steel, zinc-aluminum alloy plated steel, zinc-iron alloy plated steel, zinc-magnesium alloy plated steel, zinc-aluminum-magnesium alloy plated steel, aluminum plated steel, aluminum-silicon alloy plated steel, tin plated steel, lead-tin alloy plated steel, chromium plated steel, and nickel plated steel. In particular, the surface treating compositions are outstandingly effective when applied to plated steel members.

The method of using the surface treating composition, that is, the surface treating method may be either a method involving applying the metal surface treating composition to a member and then drying the coating, or a method involving preheating a member, applying the metal surface treating composition to the member, and allowing the coating to dry by heat inertia.

In either method, the drying conditions may include a temperature of room temperature to 250° C. and a time of 2 seconds to 1 hour and preferably a temperature of 40° C. to 180° C. and a time of 5 seconds to 20 minutes. Temperatures above 250° C. may adversely affect properties such as adhesion and corrosion resistance.

In the surface treating method, the metal surface treating composition of the invention is applied in a coating weight after drying of at least 0.1 mg/m². A coating weight of less than 0.1 mg/m² may lead to poor rust prevention. Too much buildup may be uneconomical as the pretreating agent prior to coating. The preferred coating weight is 0.5 to 500 mg/m², and more preferably 1 to 250 mg/m².

In the surface treating method, the step of applying the metal surface treating composition is not particularly limited. The composition may be applied by any of ordinary techniques such as roll coating, shower coating, spraying, dipping, and brush coating. While the steel members to be treated encompass the above-mentioned steel members, best results are obtained from the treatment of various plated steel members.

The coated steel member of the invention is produced by treating a surface of the above-mentioned steel member with the metal surface treating composition, drying the composition, and then applying an overcoat layer onto the treated steel member surface. The overcoat layer is formed by a coating system in which a non-chromate primer is optionally coated and dried before a topcoat is coated thereon, or a functional coating system having an anti-fingerprinting, lubricating or other function. The method of producing a coated steel member is applicable to not only a pre-coat steel member, but also a post-coat steel member, and the coated steel member as used herein includes both. The term "steel member" is used herein to encompass steel plates.

The non-chromate primers which can be used herein include all primer compositions which are devoid of chromate based rust-preventive pigments. Preferred primers are primers using vanadate based rust-preventive pigments and phosphate based rust-preventive pigments (V/P pigmented primers) and primers using calcium silicate based rust-preventive pigments.

The primer is preferably coated in such an amount as to give a dry coating thickness of 1 to 20 μm. A primer coating of less than 1 μm may lead to a decline of corrosion resistance whereas more than 20 μm may adversely affect the work adhesion.

The conditions for baking or drying the non-chromate primer include a metal surface temperature of 150 to 250° C. and a time of 10 seconds to 5 minutes, for example.

The topcoat used herein is not particularly limited, and any conventional coating topcoats may be used. The functional coating is not particularly limited, and all coatings which are currently applied to chromate based pretreatment coatings can be used. No particular limit is imposed on the techniques of applying the non-chromate primer, topcoat and functional coating. Use may be made of ordinary coating techniques such as roll coating, shower coating, air spraying, airless spraying, and dipping. The thickness of the topcoat may be suitably selected, i.e., the topcoat may have a typical thickness conforming to its type.

EXAMPLE

Examples and Comparative Examples are given below by way of illustration and not by way of limitation. In Examples, all parts are by weight, Me stands for methyl, and IR is an abbreviation of infrared spectroscopy.

Example 1

Method of producing organosilicon compound (5)

A 1-L separable flask equipped with a stirrer, reflux condenser, dropping funnel and thermometer was charged with 118.1 g (1 mol) of benzotriazole and 200 g of toluene and heated at 40° C. To the flask, 205.3 g (1 mol) of 3-isocyanatopropyltrimethoxysilane was added dropwise. The contents were stirred at 100° C. for 1 hour. On IR analysis, the complete disappearance of absorption peaks assigned to an isocyanate group of the reactant was observed as the end of reaction. The solvent was then removed, yielding the reaction product as a yellow liquid. By gel permeation chromatography (GPC), the reaction product was identified to be a single compound having the following formula (5).

[Chemical Formula 13]

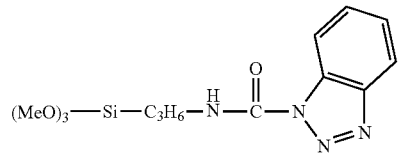

(5)

Example 2

Method of producing organosilicon compound (8)

A 1-L separable flask equipped with a stirrer, reflux condenser, dropping funnel and thermometer was charged with 133.2 g (1 mol) of 5-methylbenzotriazole and 200 g of toluene and heated at 40° C. To the flask, 205.3 g (1 mol) of 3-isocyanatopropyltrimethoxysilane was added dropwise. The contents were stirred at 100° C. for 1 hour. On IR analysis, the complete disappearance of absorption peaks assigned to an isocyanate group of the reactant was observed as the end of reaction. The solvent was then removed, yielding the reaction product as a yellow liquid. By GPC, the reaction product was identified to be a single compound having the following formula (8).

[Chemical Formula 14]

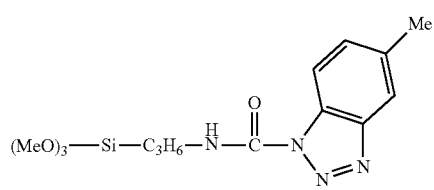

Example 3

Method of producing organosilicon compound (9)

A 1-L separable flask equipped with a stirrer, reflux condenser, dropping funnel and thermometer was charged with 133.2 g (1 mol) of 6-methylbenzotriazole and 200 g of toluene and heated at 40° C. To the flask, 205.3 g (1 mol) of 3-isocyanatopropyltrimethoxysilane was added dropwise. The contents were stirred at 100° C. for 1 hour. On IR analysis, the complete disappearance of absorption peaks assigned to an isocyanate group of the reactant was observed as the end of reaction. The solvent was then removed, yielding the reaction product as a yellow liquid. By GPC, the reaction product was identified to be a single compound having the following formula (9).

[Chemical Formula 15]

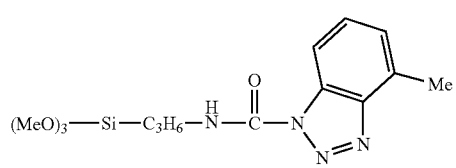

Example 4

A metal surface treating composition was prepared by adding 10 g (as nonvolatile) of organosilicon compound (5) in Example 1 to a solvent mixture of 990 g of methanol and 10 g of water and stirring them at room temperature for 5 minutes. Onto a commercial hot dip galvanized steel plate of 70×150×0.4 mm (Nippon Testpanel Co., Ltd.) which had been degreased and dried, the metal surface treating composition was applied by a bar coater No. 20 so as to form a dry coating of 10 m thick. The treated plate was dried at a metal surface temperature of 105° C. for 10 minutes. A V/P pigmented non-chromate primer was applied onto the treated plate by a bar coater No. 16 so as to form a dry coating of 5 μm thick and dried at a metal surface temperature of 215° C. for 5 minutes. A topcoat Flexicoat 1060 (polyester topcoat material, Nippon Paint Co., Ltd.) was applied onto the primer-coated plate by a bar coater No. 36 so as to form a dry coating of 15 m thick and dried at a metal surface temperature of 230° C., obtaining a test plate. The test plate was evaluated for bend-following adhesion, deep drawing resistance, and corrosion resistance by the methods described below, with the results shown in Table 1.

Examples 5 and 6

Metal surface treating compositions were prepared as in Example 4 except that the compound in Example 1 was changed to the compounds in Examples 2 and 3. Using these metal surface treating compositions, test plates were fabricated as in Example 4, and similarly evaluated. The results are shown in Table 1.

Examples 7 to 13

Metal surface treating compositions were prepared as in Example 4 except that the compound in Example 1, the type and concentration of silane compound, and the concentrations of organic titanate, water dispersible silica, zirconium ion, thiocarbonyl-containing compound, water soluble resin and phosphate ion were combined as shown in Table 1. Using these metal surface treating compositions, test plates were fabricated as in Example 4, and similarly evaluated. The results are shown in Table 1.

Comparative Examples 1 to 3

Metal surface treating compositions were prepared as in Example 4 except that the compounds in Examples 1 to 3 were not used and the type and concentration of silane compound and the concentrations of organic titanate, water dispersible silica, zirconium ion, thiocarbonyl-containing compound, water soluble resin and phosphate ion were combined as shown in Table 1. Using these metal surface treating compositions, test plates were fabricated as in Example 4, and similarly evaluated. The results are shown in Table 1.

Comparative Example 4

A test plate was fabricated as in Example 4 except that a commercial chromate treating agent for coating use (resin-containing type) was applied and dried in a chromium coating weight of 20 mg/m² instead of the metal surface treating composition, and a chromium-containing primer (a strontium chromate pigment-containing primer) was used. The test plate was similarly evaluated, with the results shown in Table 1.

Notably, the commercial products shown below were used as the silane compound, organic titanate, water dispersible silica, zirconium ion-providing compound, thiocarbonyl-containing compound, water soluble resin and phosphate ion-providing compound in Table 1.

[Silane Compound]

A: KBM-903

(γ-aminopropyltrimethoxysilane; Shin-Etsu Chemical Co., Ltd.)

B: KBM-403

(γ-glycidoxypropyltrimethoxysilane; Shin-Etsu Chemical Co., Ltd.)
C: reaction product of KBM-403 and benzotriazole (synthesized with reference to JP-A H06-279463)
[Organic Titanate]
Titanium tetraisopropoxide
[Water Dispersible Silica]
Methanol silica sol (Nissan Chemical Industries, Ltd.)
[Zirconium Ion-providing Compound]
Zircosol AC-7
(ammonium zirconium carbonate; Daiichi Kigenso Kagaku Kogyo Co., Ltd.)
[Thiocarbonyl-containing Compound]
Thiourea
[Water Soluble Resin]
Polyacrylate (weight average molecular weight 1,000,000)
[Phosphate Ion-providing Compound]
Phosphoric acid
[Evaluation Methods]
In Examples 4 to 13 and Comparative Examples 1 to 4, bend-following adhesion, deep drawing resistance and corrosion resistance were evaluated in accordance with the following methods and criteria.
Bend-following Adhesion
Using a conical mandrel tester in an environment of 20° C., the test plate was bent through 180° with interposition of a spacer of 2 mm in diameter. To the bent region, adhesive tape was applied and peeled 3 times. The degree of peeling was examined under a 20× magnifier loupe and rated according to the following criterion.

A: no cracks
B: cracks all over the bent region
C: peeled area is less than 20% of the bent region
D: peeled area is from 20% to less than 80% of the bent region
E: peeled area is at least 80% of the bent region Deep Drawing Resistance
The cupping test was performed in an environment of 20° C. under conditions: drawing ratio 2.3, blank holding pressure 2 t, punch radius 5 mm, die shoulder radius 5 mm, and oil-free. The width of peeled film from the crosscut was measured and rated according to the following criterion.

A: blister width less than 1 mm
B: blister width from 1 mm to less than 2 mm
C: blister width from 2 mm to less than 3 mm
D: blister width from 3 mm to less than 5 mm
E: blister width 5 mm or more Corrosion Resistance
(Crosscut)
A crosscut was scribed on the test plate, which was subjected to the salt spray test according to JIS Z 2371 for 500 hours. The width of blister on one side of the cut was measured and rated according to the following criterion.

A: blister width 0 mm
B: blister width from more than 0 mm to less than 1 mm
C: blister width from 1 mm to less than 3 mm
D: blister width from 3 mm to less than 5 mm
E: blister width 5 mm or more (Edge)
The test plate was subjected to the salt spray test according to JIS Z 2371 for 500 hours. The width of blister at the upper burr edge was rated according to the same criterion as in the crosscut test.

TABLE 1

| | | Formulation of metal surface treating composition | | | | | | | | | Test results | | | |
|---|---|---|---|---|---|---|---|---|---|---|---|---|---|---|
| | | Silane coupling agent | | Silane compound | | Organic titanite | Water dispersible silica | ZR ion-providing compound | Thiocarbonyl-containing compound | Water soluble resin | Phosophate ion-providing compound | Bend-following adhesion | Deep drawing reistance | Corrosion reistance | |
| | No. | Type | g/l | Type | g/l | g/l | g/l | g/l | g/l | g/l | g/l | | | Cross-Cut | Edge |
| Example | 4 | (5) | 10 | | | | | | | | | A | B | A | A |
| | 5 | (8) | 10 | | | | | | | | | A | B | A | A |
| | 6 | (9) | 10 | | | | | | | | | A | B | A | A |
| | 7 | (5) | 10 | A | 3 | | | | | | | A | B | A | A |
| | 8 | (5) | 10 | A | 3 | 4 | | | | | | A | B | A | A |
| | 9 | (5) | 10 | A | 3 | 4 | 1 | | | | | A | B | A | A |
| | 10 | (5) | 10 | A | 3 | 4 | 1 | 0.5 | | | | A | B | A | A |
| | 11 | (5) | 10 | A | 3 | 4 | 1 | 0.5 | 2.5 | | | A | B | A | A |
| | 12 | (5) | 10 | A | 3 | 4 | 1 | 0.5 | 2.5 | 25 | | A | A | A | A |
| | 13 | (5) | 10 | A | 3 | 4 | 1 | 0.5 | 2.5 | 25 | 0.5 | A | A | A | A |
| Comparative Example | 1 | | | A | 10 | 4 | 1 | 0.5 | 2.5 | 25 | 0.5 | E | E | D | D |
| | 2 | | | B | 10 | 4 | 1 | 0.5 | 2.5 | 25 | 0.5 | E | E | D | D |
| | 3 | | | C | 10 | 4 | 1 | 0.5 | 2.5 | 25 | 0.5 | C | C | B | B |
| | 4 | chromate treating agent for coating use | | | | | | | | | | C | C | B | C |

The results of Examples and Comparative Examples demonstrate that the metal surface treating composition of the invention forms a coating which exhibits good rust prevention and tight adhesion to substrates.

The invention claimed is:

1. A method for producing an organosilicon compound having the general formula (1):

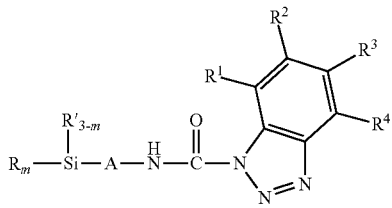
(1)

wherein R is a hydrolyzable group, R' is a $C_1$-$C_4$ alkyl group, A is a $C_1$-$C_8$ alkylene group, $R^1$, $R^2$, $R^3$ and $R^4$ are each independently hydrogen or a $C_1$-$C_6$ alkyl group when they do not form a ring structure, or a pair of $R^1$ and $R^2$, $R^2$ and $R^3$, or $R^3$ and $R^4$ may bond together to form an aliphatic or aromatic ring structure, and m is an integer of 1 to 3, comprising the step of reacting an organosilicon compound having the general formula (3):

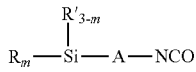
(3)

wherein R, R', A and m are as defined above, with a benzotriazole compound having the general formula (4):

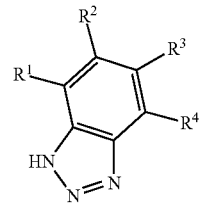
(4)

wherein $R^1$, $R^2$, $R^3$ and $R^4$ are as defined above.

2. The method of producing an organosilicon compound of claim 1, having the general formula (2):

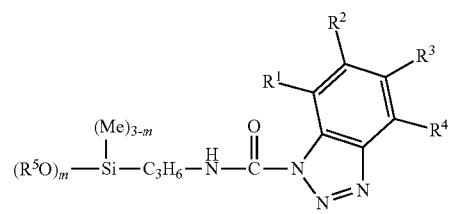
(2)

wherein $R^5$ is a $C_1$-$C_{10}$ alkyl or $C_6$-$C_{10}$ aryl group, $R^1$, $R^2$, $R^3$, $R^4$ and m are as defined above, and Me is methyl.

* * * * *